United States Patent [19]
Koide et al.

[11] Patent Number: 5,550,041
[45] Date of Patent: * Aug. 27, 1996

[54] CAFFEINE DEMETHYLATE GENE-CONTAINING DNA FRAGMENT AND MICROBIAL PROCESS FOR PRODUCING 3-METHYL-7-ALKYLXANTHINE

[75] Inventors: Yoshinao Koide; Seiji Nakane; Yutaka Imai, all of Aichi, Japan

[73] Assignee: Amano Pharmaceutical Co., Ltd., Nagoya, Japan

[ * ] Notice: The portion of the term of this patent subsequent to Apr. 14, 2012, has been disclaimed.

[21] Appl. No.: 324,483

[22] Filed: Oct. 18, 1994

Related U.S. Application Data

[63] Continuation of Ser. No. 63,553, May 18, 1993, abandoned.

[30] Foreign Application Priority Data

May 20, 1992 [JP] Japan ..................................... 4-154380
Oct. 27, 1992 [JP] Japan ..................................... 4-312954

[51] Int. Cl.⁶ ..................... C12P 17/18; C12N 9/14; C12N 9/78; C12N 1/21
[52] U.S. Cl. .................... 435/119; 435/118; 435/195; 435/227; 435/252.3; 435/252.34; 435/320.1; 435/172.3; 536/23.2; 935/60; 930/240
[58] Field of Search ..................... 435/119, 118, 435/195, 227, 252.3, 252.34, 320.1, 172.3, 874, 875, 876, 877; 935/60; 930/240; 536/23.2

[56] References Cited

U.S. PATENT DOCUMENTS 4,228,191 10/1980 Haas et al. ................................ 426/45
4,675,285 1/1987 Clark et al. ................................ 435/6

FOREIGN PATENT DOCUMENTS 0509834 10/1992 European Pat. Off. .

OTHER PUBLICATIONS

Hohnloser et al. 1980 Hoppe–Seyler's Z. Physiol. Chem., Bd 361, S. 1763–1766.
Itoh et al. 1991. J. Biochem. 110, 614–621.
Patent Abstracts of Japan, vol. 9(78), C–274, 1801, Apr. 6, 1985.
Watson et al., 1987, in: *Molecular Biology of the Gene*, Fourth Edition, Benjamin/Cummings Publishing Company, Inc., Menlo Park, CA, p. 313.

*Primary Examiner*—Christopher S. F. Low
*Attorney, Agent, or Firm*—Sughrue, Mion, Zinn, Macpeak & Seas

[57] ABSTRACT

A DNA fragment containing a caffeine demethylase gene produced by a microorganism belonging to the genus Pseudomonas and capable of assimilating caffeine and a process for producing a 3-methyl-7-alkylxanthine comprising cultivating a novel bacterium strain of the genus Pseudomonas having been transformed with a recombinant DNA having integrated therein the above-mentioned DNA fragment in a nutrient culture medium containing a 1,3-dimethyl-7-alkylxanthine to produce a 3-methyl-7-alkylxanthine in the culture and recovering the produced 3-methyl-7-alkylxanthine from the culture are disclosed, as well as a process for producing 3-methyl-7-propylxanthine, comprising cultivating a microorganism capable of converting 1,3-dimethyl-7-propylxanthine to 3-methyl-7-propylxanthine or a mutant thereof in a nutrient culture medium containing 1,3-dimethyl-7-propylxanthine, to produce 3-methyl-7-propylxanthine in the culture and recovering the produced 3-methyl-7-propylxanthine from the culture.

10 Claims, 2 Drawing Sheets

CAFFEINE DEMETHYLATE GENE-CONTAINING DNA FRAGMENT AND MICROBIAL PROCESS FOR PRODUCING 3-METHYL-7-ALKYLXANTHINE

This is a continuation of application Ser. No. 08/063,553 filed May 18, 1993, abandoned.

FIELD OF THE INVENTION

This invention relates to a DNA fragment containing a caffeine demethylase gene produced by a microorganism belonging to the genus Pseudomonas and capable of metabolizing caffeine; a novel strain of the genus Pseudomonas obtained by transformation with a recombinant DNA containing said DNA fragment; and a microbial process for producing a 3-methyl-7-alkylxanthine.

BACKGROUND OF THE INVENTION

3-Methyl-7-alkylxanthines are important intermediates for pharmaceuticals. For example, 3,7-dimethylxanthine (theobromine) is an important intermediate for 1-(5-oxohexyl)-3,7-dimethylxanthine (pentoxyfylline), and 3-methyl-7-propylxanthine is an important intermediate for 1-(5-oxohexyl)-3-methyl-7-propylxanthine (propentophylline).

3,7-Dimethylxanthine has conventionally been produced by extraction from cocoa beans or by synthesis from 3-methylurea.

Propentophylline, which is useful as a drug for treating cerebrovascular disorders, has generally been synthesized by the introduction of a 5-oxohexyl group into 3-methyl-7-propylxanthine as disclosed in JP-B-52-33120 (the term "JP-B" as used herein means an "examined Japanese patent publication"). The starting material 3-methyl-7-propylxanthine can be synthesized through various chemical processes. A typical example is a process comprising treating 1,3-dimethyl-7-propylxanthine with an alkali to obtain 4-methylamino-5-methylcarbamoyl-1-propylimidazole, which is reacted with urea to obtain N-methyl-N-(5-methylcarbamoyl-1-propylimidazol-4-yl)urea, followed by cyclization as disclosed in JP-A-1-180883 (the term "JP-A" as used herein means an "unexamined published Japanese patent application"). However, these known chemical synthesis processes have many problems in their application to industrial production, including involvement of very complicated steps. Therefore, it is desirable to develop a simpler process for synthesizing 3-methyl-7-propylxanthine.

Further, microbial techniques for synthesizing 3,7-dimethylxanthine have been studied. For example, converting 1,3,7-trimethylxanthine (caffeine) into 3,7-dimethylxanthine by using a microorganism capable of assimilating caffeine or a mutant strain thereof was suggested in *Hoope-Seyler's Z. Physiolo. Chem.*, Vol. 358, p. 807 (1977), JP-B-4-12117, and EP-A-0509834.

However, microbial synthesis of a 3-methyl-7-alkylxanthine other than 3,7-dimethylxanthine is unknown. In addition, the known microbial processes for synthesizing 3,7-dimethylxanthine are still unsatisfactory for carrying out on an industrial scale from the standpoint of conversion efficiency, and the like.

SUMMARY OF THE INVENTION

In the light of the above circumstances, the present inventors extensively searched for a microorganism capable of site-specifically demethylating a 1,3-dimethyl-7-alkylxanthine and unexpectedly found that a strain belonging to the genus Pseudomonas, previously isolated from nature by the present inventors, and capable of assimilating caffeine, when cultivated in a nutrient culture medium containing a 1,3-dimethyl-7-alkylxanthine, produces a corresponding 3-methyl-7-alkylxanthine in the culture.

The present inventors previously obtained a mutant strain constitutively metabolizing caffeine by mutation of a microorganism assimilating caffeine isolated from soil and also obtained a double mutated strain therefrom by further mutating the microorganism to that it lacks the ability to demethylate theobromine into 7-methylxanthine (see EP-A-0509834).

The present inventors have found that the above-mentioned double mutant strain has a more potent ability to produce a 3-methyl-7-alkylxanthine from the corresponding 1,3-dimethyl-7-alkylxanthine than the parent strain isolated from nature.

If the reaction in the first step of the caffeine metabolic pathway by the above-described microorganism could be conducted more efficiently, the ability of producing a 3-methyl-7-alkylxanthine from a corresponding 1,3-dimethyl-7-alkylxanthine would be further increased. With this expectation, the present inventors have conducted further investigation in an attempt to enhance the activity of caffeine demethylase which is understood to catalyze the reaction. As a result, they have succeeded in cloning the gene of caffeine demethylase of which no proteological knowledge had been known. The present invention has been completed based on these findings.

Figure 1:
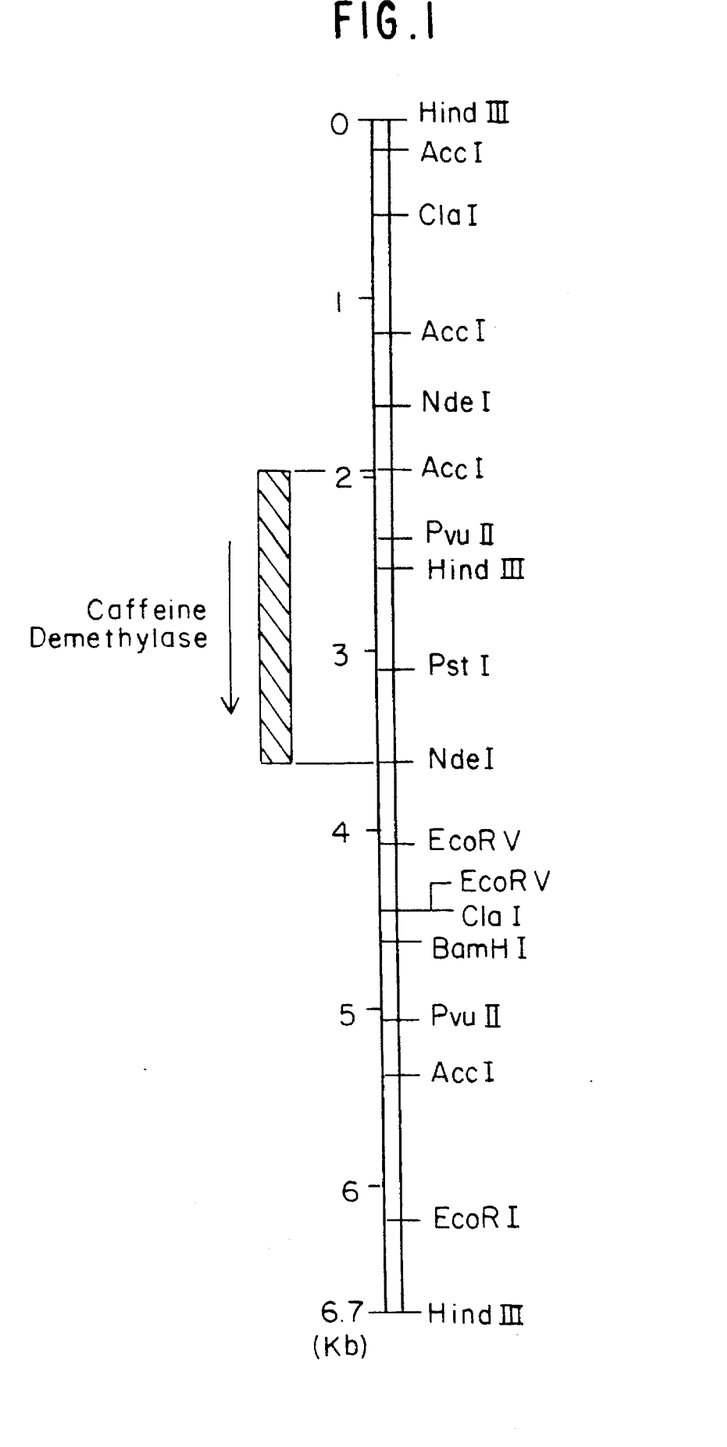
FIG. 1 is a restriction endonuclease cleavage map of DNA fragment containing a caffeine demethylase gene.

The present invention provides:

(1) an isolated and purified DNA fragment containing a caffeine demethylase gene derived from a bacterium belonging to the genus Pseudomonas.;

(2) a DNA fragmentsaccording to (1) above which is specified by the restriction endonuclease cleavage map shown in FIG. 1;

(3) a DNA fragment according to (2) above, in which the base sequence between the AccI site and the NdeI site, which contains the caffeine demethylase gene, is represented by SEQ ID NO:1;

(4) an isolated and purified DNA fragment containing a base sequence which encodes the amino acid sequence of SEQ ID NO:2.

(5) a recombinant DNA having integrated in the vector thereof the DNA fragment according to (1) or (4) above;

(6) a novel bacterial strain of the genus Pseudomonas comprising a host transformed with the recombinant DNA according to (5) above;

(7) a novel bacterial strain of the genus Pseudomonas of (6) above, in which the host is *Pseudomonas putida*; and (8) a novel bacterial strain of the genus Pseudomonas according to (7) above, in which the host is *Pseudomonas putida* IF-3-9C-21.

The present invention also provides a process for producing 3-methyl-7-alkylxanthine comprising cultivating a microorganism transformed with a recombinant DNA containing a caffeine demethylase gene in a nutrient culture medium containing 1,3-dimethyl-7-alkylxanthine to produce a corresponding 3-methyl-7-alkylxanthine in the culture and recovering the produced 3-methyl-7-alkylxanthine from the culture.

The present invention further provides a process for producing 3-methyl-7-propylxanthine, comprising cultivating a microorganism of the Pseudomonas strain capable of converting 1,3-dimethyl-7-propylxanthine to 3-methyl-7-propylxanthine or a mutant derived therefrom in a nutrient culture medium containing 1,3-dimethyl-7-propylxanthine to produce 3-methyl-7-propylxanthine in the culture and recovering the produced 3-methyl-7-propylxanthine from the culture.

DETAILED DESCRIPTION OF THE INVENTION

The microorganisms which can be used in the present invention include those capable of converting a 1,3-dimethyl- 7-alkylxanthine represented by formula (I):

wherein R represents a straight-chain or branched alkyl group, into a 3-methyl-7-alkylxanthine represented by formula (II):

wherein R is as defined above.

In the present invention, R in the above formulae (I) and (II) is preferably a $C_1$–$C_4$ alkyl group.

The above-mentioned microorganisms include bacteria belonging to the genus Pseudomonas and mutants derived therefrom. Specific examples are *Pseudomonas putida* IF-3 (deposited as FERM BP-3824 under the Budapest Treaty) isolated from soil, which is described in EP-A-0,509,834, Pseudomonas sp. 188-1 (deposited as FERM P-7073, FERM BP-4282 under the Budapest Treaty) described in JP-B-4-12117, and mutants of these strains.

According to the present inventors' research, Pseudomonas sp. 188-1 (deposited as FERM P-7073, FERM BP-4282 under the Budapest Treaty) was identified as *Pseudomonas cepacia* as hereinafter described. Pseudomonas sp. 188-1 (deposited as FERM P-7073, FERM BP-4282 under the Budapest Treaty) will hereinafter be called *Pseudomonas cepacia* FERM BP-4282.

Mutation to obtain mutant strains from above strains can be carried out according to known methods, such as a chemical treatment with N-methyl-N'-nitro-N-nitrosoguanidine (hereinafter abbreviated as NTG) as a mutagen. In addition, 2-aminopurine, 5-bromouracil, ethyl methanesulfonate, dimethyl sulfate, acriflavine, Acridine Orange, hydrazine, 4 -nitroquinoline-N-oxide, manganese chloride, and the like may also be used as a mutagen. Mutation can also be induced by physical means using ultraviolet irradiation or radioactive irradiation by X-rays, γ-rays, etc. (cf. *The Molecular Basis of Mutation*, John W. Drake (1970), Holden-Day. Inc. and *General Genetics* (2nd. Edition), W. H. FREEMAM AND COMPANY).

The mutant strains can be isolated by known procedures, such as a direct method in which a microorganism having been subjected to the mutation treatment is cultured, and each colony is examined for the occurrence of mutation; a replica method as a modification of the above method; a condensation method using antibiotics such as penicillin; and an appropriate combination of these methods.

In the present invention, the following experimental procedures were taken in selection of strains capable of converting a 1,3-dimethyl-7-alkylxanthine into a 3-methyl-7-alkylxanthine. About 100 caffeine-resistant strains were isolated from soil and capable of growing on an agar medium containing 1.0% Bacto-peptone, 0.5% Bacto-yeast extract, 0.5% sodium chloride, and 2.0% caffeine and were each inoculated on to an agar medium (pH=7.0) containing 0.3% caffeine, 0.3% ammonium sulfate, 0.5% potassium secondary phosphate, 0.1% sodium chloride, and 0.2% magnesium sulfate and cultured at 30° C. for 3 days, and those strains showing excellent growth were selected.

The bacteriological properties of *Pseudomonas putida* IF-3 and *Pseudomonas cepacia* FERM BP-4282 are as follows. These bacteriological properties were examined according to *Manual of the Identification of Medical Bacteria* (MIMB), *Identification of Microorganisms* published by Society of Hygienic Technology, Japan, and *Classification and Identification of Microorganisms*, Vol. II, published by Academic Society Press Center, Japan.

*Pseudomonas putida* IF-3 a. Morphological Properties:
1) Gram's stain: negative
2) Form and size of cell: rod of about 0.8×2–3 μm
3) Presence of Motility: positive
4) Flagellum: >1
5) Formation of spores: negative b. Physiological Properties:
1) O-F test (the Hugh-Leifson method): aerobic acid production
2) Hemolysis: positive
3) Behavior to oxygen: aerobic
4) Acid production from sugars:

| | |
|---|---|
| D-glucose | + |
| D-xylose | + |
| mannitol | − |
| lactose | − |
| sucrose | − |
| D-maltose | − |
| D-fructose | − |
| L-arabinose | + |
| raffinose | − |
| inulin | − |
| salicin | − |
| Sepharose | − |

| | |
|---|---|
| D-sorbitol | − |
| D-galactose | + |
| glycerol | − |

5) Catalase test: positive
6) Oxidase test: positive
7) Growth on MacConkey's medium: positive
8) Growth on SS agar medium: positive
9) Hydrolysis of DBH: negative
10) Accumulation of PHB: negative
11) Utilization of citric acid: positive
12) Decomposition of urea: negative
13) Nitrate Reduction: positive
14) Denitirification reaction: negative
15) Heat resistance (60° C.×30 mins): not resistant
16) Growth temperature:
   growth at 5° C.
   growth at 25° C.
   growth at 37° C.,
   no growth at 42° C.
17) Hydrolysis of gelatin: negative
18) Litmus milk reaction: positive
19) Hydrolysis of starch: negative
20) Hydrolysis of casein: negative
21) Lectinase reaction: negative
22) Decarboxylation of lysine: negative
23) Arginine dihydrolase: positive
24) Decarboxylation of ornithine: negative
25) Hydrolysis of esculin: negative
26) NaCl resistance:
   resistant to 0% NaCl
   resistant to 4% NaCl
   no resistant to 6% NaCl
   no resistant to 7% NaCl
27) Acylamidase: negative
28) Oxidation of gluconic acid: negative
29) Presence of DNAase: negative
30) Pigment Production:
   in King A medium: negative
   in King B medium: positive
31) Hydrolysis of TW-80: negative
32) Growth in NAC medium: positive
33) Hydrolysis of agar: negative
34) Levan production from sucrose: negative
35) Deamination of phenylalanine: negative
36) Growth in Methylene Blue milk:
   decrease in Methylene Blue: positive
   coagulation of Methylene Blue: negative
   Peptonization: negative
37) Acid from TSI: negative/negative
38) Hydrogen sulfide production in TSI medium: negative
39) Hydrolysis of sodium hippurate: positive
40) MR test: negative
41) VP test: negative Discrimination of the strain was made based on the above bacteriological properties according to Guide to Presumptive Identification and Bergey's Manual of Systematic Bacteriology. From the results of the number of flagella, growth at 42° C., hydrolysis of gelatin and TW-80, acid production from trehalose and mannitol, and the like, the strain was identified to belong to the species *Pseudomonas putida* and designated as *Pseudomonas putida* IF-3. The strain was deposited to National Institute of Bioscience and Human-technology, Agency of Industrial Science & Technology, MITI, 1-3, Higashi 1-chome, Tsukuba-shi, Ibaraki-ken 305, Japan under the accession number of FERM BP-3824 under the Budapest Treaty.

*Pseudomonas cepacia* BP-4282 a. Morphological Properties:
   1) Gram's stain: negative
   2) Form and size of cell: short rod of about 0.7–0.8× 1.0–1.3 μm
   3) Presence of Motility: positive
   4) Flagellum: >1
   5) Formation of spores: negative b. Physiological Properties:
   1) O-F test (the Hugh-Leifson method): aerobic acid production
   2) Behavior to oxygen: strictly aerobic
   3) Acid production from sugars:

| | |
|---|---|
| L-arabinose | + |
| D-xylose | + |
| D-glucose | + |
| D-mannose | + |
| D-fructose | + |
| D-galactose | + |
| maltose | + |
| sucrose | + |
| lactose | + |
| trehalose | + |
| D-sorbitol | + |
| D-mannitol | + |
| glycerol | + |
| inositol | − |

4) Catalase test: weakly positive
5) Oxidase test: positive
6) Utilization of citric acid (in both Koser's medium and Christensen's medium): positive
7) Nitrate reduction: positive
8) Heat resistance (60° C.×30 mins): not resistant
9) Growth temperature: grow at 9° to 41° C.
10) Hydrolysis of gelatin: negative
11) Litmus milk reaction: negative
12) Hydrolysis of starch: negative
13) Decarboxylation of lysine: positive
14) Arginine dihydrolase: negative
15) Decarboxylation of ornithine: negative
16) Acylamidase: positive
17) Oxidation of gluconic acid: positive
18) Pigment Production:
   in King A medium: negative
   in King B medium: negative
19) MR test: negative
20) VP test: negative Discrimination of the strain was made based on the above bacteriological properties according to Bergey's Manual of Systematic Bacteriology. From the results illustrating the presence of Gram's negative bacteria, rod shape, motility with polar flagella, aerobic property, oxidase positive, and acid production from glucose, the strain was classified in the genus Pseudomonas. The strain was initially named Pseudomonas sp. 188-1 and deposited with the National Institute of Bioscience and Human-technology, Agency of Industrial Science & Technology, MITI, 1-3, Higashi 1-chome, Tsukuba-shi, Ibaraki-ken 305, Japan under the accession number of FERM P-7073 (FERM BP-4282 under the Budapest Treaty).

As a result of a follow-up study, this strain was identified to belong to the species *Pseudomonas cepacia* from its negative ornithine decarboxylase activity, positive lysine decarboxylase activity, positive gluconic acid oxidase activity, positive acylamidase activity, negative arginine dihydrolase activity, and growth at 41° C.

Further, the present inventors have already obtained a mutant *Pseudomonas putida* IF-3-9C-21 from the parent strain *P. putida* IF-3. The strain IF-3-9C-21 is capable of constitutively converting caffeine into theobromine but incapable of converting theobromine into 7-methylxanthine. The strain has been deposited at National Institute of Bioscience and Human-technology, Agency of Industrial Science & Technology, MITI, 1-3, Higashi 1-chome, Tsukuba-shi, Ibaraki-ken 305, Japan under the accession number of FERM BP-3825 under the Budapest Treaty.

Caffeine metabolism by bacteria of the genus Pseudomonas is considered to proceed as follows (see *Hoope-Seyler's Z. Physiol. Chem.*, Vol. 358, pp. 807–817 (1977)).

Caffeine (1,3,7-trimethylxantbine) $\downarrow$ ← Step 1

Theobromine (3,7-dimethylxanthine) $\downarrow$ ← Step 2

7-Methylxanthine $\downarrow$ ← Step 3

Xanthine

In Steps 1, 2 and 3, it is thought that enzymes specifically release the methyl groups at the 1-, 3-, and 7-positions, respectively. However, having no knowledge of the proteological properties of these enzymes, such as molecular weight, isoelectric point, amino acid sequence, amino acid composition, etc., the existence thereof has not yet been proteologically confirmed.

For the purpose of enhancing the activity of caffeine demethylase in the above-mentioned microorganisms, the present inventors made a successful attempt to clone the gene of caffeine demethylase.

The DNA fragment, recombinant DNA, and transformed microorganisms according to the present invention can be obtained basically through the following steps.

(1) Preparation of a host for caffeine demethylase gene cloning. *Pseudomonas putida* IF-3-9C capable of metabolizing caffeine is subjected to a mutation treatment, and a strain capable of assimilating theobromine but incapable of assimilating caffeine (*Pseudomonas putida* IF-3-19) is isolated.

(2) The total DNA is extracted from *Pseudomonas putida* IF-3 (deposited as FERM BP-3824 under the Budapest Treaty) and partially cleaved with appropriate restriction enzymes (e.g., HindIII).

(3) The DNA fragments obtained in (2) is inserted and ligated to pNI20C at the HindIII recognition site to provide a recombinant DNA.

(4) *Pseudomonas putida* IF-3-19 obtained in (1) is transformed by using the recombinant DNA obtained in (3) to provide a transformant strain having restored caffeine assimilability.

(5) The recombinant DNA is subcloned, and the base sequence of the DNA fragment is determined to identify the coding area of caffeine demethylase.

(6) A DNA fragment of appropriate size which contains the entire coding area of caffeine demethylase (a fragment which is assumed to contain the promotor, terminator, etc. of the gene) is integrated into a vector (pNI107: a vector known for its ability to transform a bacterium of the genus Pseudomonas) to obtain a recombinant DNA.

(7) *Pseudomonas putida* IF-3-9C-21 (deposited as FERM BP-3825 under the Budapest Treaty) is transformed by using the recombinant DNA obtained in (6).

(8) The ability of the transformant obtained in (7) to convert a 1,3-dimethyl-7-alkylxanthine to a 3-methyl-7-alkylxanthine is confirmed.

The above-described recombinant DNA experiment can easily be carried out in accordance with known procedures commonly employed in genetic engineering, for example, the procedures described in Maniatis, et al., *Molecular Cloning: A Laboratory Manual*, Cold Spring Harber Laboratory (1989). All the enzymes and reagents used in the experiment are commercially available. So long as the use conditions specified for the particular product are met, the intended object can completely be accomplished, except where noted.

For example, the source of DNA used in (2) above includes *Pseudomonas putida* IF-3 (deposited as FERM BP-3824 under the Budapest Treaty) and *Pseudomonas flayida* IF-4 (deposited as FERM P-10865, FERM BP-4281 under the Budapest Treaty).

The bacteriological properties of *Pseudomonas flavida* are as follows. These bacteriological properties were examined according to *Manual of the Identification of Medical Bacteria* (MIMB), *Identification of Microorganisms* published by Society of Hygienic Technology, Japan, and *Classification and Identification of Microorganisms*, Vol. II, published by Academic Society Press Center, Japan.

*Pseudomonas flayida* IF-4 a. Morphological Properties:

1) Gram's stain: negative
2) Form and size of cell: short rod of about 0.7–1.1× 1.1–2.5 μm
3) Presence of Motility: positive
4) Flagellum: >1
5) Formation of spores: negative b. Physiological Properties:

1) O-F test (the Hugh-Leifson method): aerobic acid production
2) Behavior to oxygen: aerobic
3) Acid production from sugars:

| D-glucose | + |
|---|---|
| D-xylose | + |
| mannitol | − |
| lactose | − |
| sucrose | − |
| maltose | − |
| salicin | − |
| D-fructose | + |

4) Catalase test: positive
5) Cytochrome oxidase test: negative
6) Growth on MacConkey's medium: positive
7) Growth on SS agar medium: positive 8) Utilization of citric acid: positive
9) Decomposition of urea: negative
10) Nitrate Reduction: negative
11) Denitirification reaction: negative
12) Growth temperature:
   growth at 5° C.
   no growth at 41° C.
13) Hydrolysis of gelatin: positive
14) Litmus milk reaction: alkaline
15) Hydrolysis of starch: negative
16) Hydrolysis of casein: negative
17) Lectinase reaction: negative
18) Decarboxylation of lysine: negative
19) Arginine dihydrolase: positive
20) Decarboxylation of ornithine: negative
21) Hydrolysis of esculin: negative
22) NaCl resistance:
   resistant to 6% NaCl
23) Acylamidase: negative
24) Oxidation of gluconic acid: positive
25) Presence of DNAase: negative
26) Pigment Production:
   in Trypto Soy-agar medium: positive
   in King B medium: positive
27) Hydrolysis of TW-80: negative
28) Growth in NAC medium: positive
29) Hydrolysis of agar: negative
30) Levan production from sucrose: negative
31) Deamination of phenylalanine: negative
32) Acid from TSI: negative/negative
33) MR test: negative
34) VP test: negative Determination of the type of strain was made based on the above bacteriological properties according to the Guide to Presumptive Identification and Bergey's Manual of Systematic Bacteriology. It is apparent that the strain belongs to the genus Pseudomonas form this analysis. From species determination, however, the strain was judged to belong to none of the conventionally known species since no description of the strain is found in any of the conventional manuals and that it possesses a novel plasmid pNI10 and pNI20. The strain was named *Pseudomonas flayida* IF-4 for the gloss and yellow color. The strain was deposited in the National Institute of Bioscience and Human-technology, Agency of Industrial Science & Technology, MITI, 1-3, Higashi 1-chome, Tsukuba-shi, Ibaraki-ken 305, Japan under the accession number of FERM P-10865 (FERM BP-4281 under the Budapest Treaty).

Extraction of the total DNA from the bacterium can be carried out, for example, in accordance with the Saito's method (see *Biochem. Biophys. Acta.*, vol. 72, pp. 619–629 (1963)).

Sequence determination of DNA in (5) can be made, for example, in accordance with the conventional dideoxy method (see *Proc. Natl. Acad. Sci.*, U.S.A., Vol. 73, p. 5463 (1977)).

Vectors which can be used for transformation of *Pseudomonas putida* in (3) and (6) include plasmids pNI107 and pNI20C (see JP-A-3-67590, JP-A-3-67591, and *Journal of Biochemistry*, Vol. 110, pp. 614–621 (1991)).

Transformation of *Pseudomonas putida* in (7) can be effected, for example, in accordance with the method of Bagdasarian et al. (see *Gene,* Vol. 16, p. 237 (1981)).

Microorganisms other than *Pseudomonas putida* can also be used as a host by using an appropriate vector. For example, other Pseudomonas species as described in *J. Biochem.*, Vol. 110, pp. 614–621 (1991), etc. are preferably used.

In carrying out the process for producing a 3-methyl-7-alkylxanthine according to the present invention, the above-mentioned microorganisms and transformants thereof are preferably used. In particular, mutants of *Pseudomonas putida* IF-3, especially *Pseudomonas putida* IF-3-9C-21, and the transformants thereof, are preferred.

Any nutrient medium may be used for culturing the strain as long as the microorganism can grow therein. The medium may be either a natural medium or a synthetic medium which contains routine components, such as carbon sources besides a 1,3-dimethyl-7-alkylxanthine, nitrogen sources, inorganic salts, and if desired, other nutrients and auxiliary components (e.g., pH regulator, emulsifying agent, anti-foaming agent, etc.). Suitable carbon sources other than the 1,3-dimethyl-7-alkylxanthine include sugars, e.g., glucose, xylose, and arabinose; sugar alcohols, e.g., glycerol and sorbitol; and organic acids, e.g., citric acid and fumaric acid. Suitable nitrogen sources include inorganic nitrogen sources, e.g., ammonium salts and nitrates; and organic nitrogen sources, e.g., meat extract, yeast extract, tryptone, and caltivator. Suitable inorganic salts include potassium phosphate, potassium chloride, magnesium sulfate, sodium chloride, sodium phosphate, and ferrous sulfate.

The concentration of 1,3-dimethyl-7-alkylxanthine in the medium is not particularly limited and decided from the desired yield of 3-methyl-7-alkylxanthine and the culture conditions as well as from an economical standpoint. The concentration usually ranges from 0.1 to 10% and is preferably from 0.5 to 5.0%. The culturing is conducted at a temperature of from 10° to 40° C. and a pH of from about 4.5 to 9.0, preferably at a temperature of from 20° to 30° C. at a pH of from 6.5 to 7.5, desirably for a period of from 5 to 72 hours. By continuously feeding the medium containing carbon sources, e.g., glucose and xylose, and nitrogen sources, e.g., meat extract, yeast extract, and sodium glutamate, while controlling the-concentration of the 1,3-dimethyl-7-alkylxanthine in the medium, the conversion reaction of 1,3-dimethyl-7-alkylxanthine to the corresponding 3-methyl-7-alkylxanthine continuously occurs (feed batch culture). The 1,3-dimethyl-7-alkylxanthine may be added either as a solid or as an aqueous solution.

If desired, a reaction accelerator which accelerates accumulation of the 3-methyl-7-alkylxanthine in the culture may be added. Suitable examples of such a reaction accelerator include monomethylxanthine, metallic ions (e.g., a nickel ion or a zinc ion), caffeine, and theobromine, although the type of accelerator used varies on the strain in the culture.

In carrying out the present invention, the product may be derived from the culture itself as obtained by the above-described culturing and culture products, such as the microbial cells, the culture filtrate, the disrupted cells, the lyophilized cells, the cell extract with a solvent, e.g., ethyl alcohol, toluene or ethyl ether, and the immobilized cells.

The 1,3-dimethyl-7-alkylxanthine is converted into the corresponding 3-methyl-7-alkylxanthine when brought into contact with the culture or the culture product in an aqueous medium. The 1,3-dimethyl-7-alkylxanthine may be present in a suspended state in the reaction system, i.e., in a concentration exceeding its solubility. The contact of the 1,3-dimethyl-7-alkylxanthine with the culture or culture product may be effected in a batch system or in a continuous system using a column.

The mixture of the culture or culture product and the 1,3-dimethyl-7-alkylxanthine is stirred with aeration under the above-mentioned conditions for 5 to 80 hours to continue the conversion reaction under aerobic conditions. The thus produced 3-methyl-7-alkylxanthine can be recovered from the reaction mixture in a usual manner. That is, the reaction mixture, if desired after centrifugal separation, is treated with an alkali, and any impurities are removed with an organic solvent, followed by pH adjustment to give the 3-methyl-7-alkylxanthine as a precipitate.

The present invention will now be illustrated in greater detail with reference to Reference Examples and Examples, but it should be understood that the present invention is not construed as being limited thereto.

REFERENCE EXAMPLE 1

Synthesis of 1,3-Dimethyl-7-propylxanthine 600 g of theophylline (a product of Katayama Kagaku Kogyo K.K.) was dissolved in 180 ml of an aqueous solution containing 263.4 g of potassium hydroxide, and the solution was evaporated to dryness under reduced pressure to prepare a potassium salt of theophylline. The resulting salt was suspended in 3600 ml of dimethylformamide, and 436.5 ml of propyl bromide was added thereto, followed by heating at 90° C. for 8 hours while stirring. Dimethylformamide was removed by distillation under reduced pressure, and to the residue was added 1800 ml of dichloromethane. The mixture was washed three times with 300 ml portions of a 1N potassium hydroxide aqueous solution and then once with 300 ml of water and dried over 54 g of anhydrous magnesium sulfate. The desiccant was removed by filtration, and the mother liquor was dried under reduced pressure and then in vacuo (85° C., 5 hours) to obtain 657 g (yield: 88.8%) of 1,3-dimethyl-7-propylxanthine.

REFERENCE EXAMPLE 2

Preparation of *Pseudomonas putida* IF-3-9C-21

*Pseudomonas putida* IF-3 (FERM BP-3824) was cultured in a TY medium (a product of Difco Co.; containing 1.0% Bacto-tryptone and 0.5% Bacto-yeast extract) to the logarithmic growth phase, and the microbial cells were collected by centrifugation, washed, and suspended in 5 ml of a 50 mM Tris-maleate buffer (pH=6.0).

NTG was added to the cell suspension to a concentration of 100 μg/ml, and the suspension was allowed to stand at 30° C. for 30 minutes. After the NTG treatment, the cells were washed twice with a 0.9% sodium chloride aqueous solution, suspended in a TY medium, followed by shake culturing at 30° C. overnight. The cells were collected by centrifugation, washed twice with a 0.9% sodium chloride aqueous solution, and further cultured in 5 ml of a caffeine minimal medium (0.3% ammonium sulfate, 0.5% potassium secondary phosphate, 0.1% sodium chloride, 0.2% magnesium sulfate heptahydrate, and 0.1% caffeine; pH=7.0) at 30° C. for 6 hours. The resulting culture was diluted and spread on a caffeine minimal agar medium (0.3% ammonium sulfate, 0.5% potassium secondary phosphate, 0.1% sodium chloride, 0.2% magnesium sulfate heptahydrate, 0.1% caffeine, and 1.5% agar; pH=7.0). After culturing at 30° C. for 2 days, the colonies were screened for strains showing excellent growth.

Each mutant strain thus obtained was inoculated to an LKC medium (1.0% Bacto-tryptone, 0.5% Bacto-yeast extract, 0.5% sodium chloride, 0.5% potassium secondary phosphate, and 0.1% caffeine; pH=7.0). After culturing at 30° C. for 8 hours, the caffeine concentration in the medium was measured. A strain which showed a higher caffeine decrease as compared with the parent strain was isolated as the constitutive mutant strain in caffeine metabolism, designated strain 9C.

Strain 9C was treated with NTG in the same manner as described above. The collected and washed microbial cells were shake cultured at 30° C. overnight in a theobromine minimal medium containing 0.3% theobromine, the same inorganic salts as in the caffeine minimal medium, and 300 μg/ml of carbenicillin. The cells were washed twice with a 0.9% sodium chloride aqueous solution and diluted and spread on an LT-agar medium (1.0% Bacto-tryptone, 0.5% Bacto-yeast extract, 0.3% theobromine, and 1.5% agar; pH=6.8), followed by culturing at 30° C. fox 2 days to form colonies. Twenty-five colonies, which did not decompose theobromine around the colonies, were obtained.

The assimilation properties for caffeine, theobromine, and 7-methylxanthine of the isolated strains were examined, and a strain which had assimilated only 7-methylxanthine, designated *Pseudomonas putida* IF-3-9C-21 (deposited as FERM BP-3825 under the Budapest Treaty), was isolated. The strain *Pseudomonas putida* IF-3-9C-21 is a double mutant which constitutively assimilates caffeine but does not convert theobromine into 7-methylxanthine.

EXAMPLE 1

*Pseudomonas putida* IF-3-9C-21 (deposited as FERM BP-3825 under the Budapest Treaty) was inoculated to 75 ml of a medium containing 1.0% 1,3-dimethyl-7-propylxanthine prepared in Reference Example 1, 1.0% of Bacto-tryptone, 0.5% Bacto-yeast extract, and 1.0% potassium secondary phosphate (pH=6.7) in a 500 ml Sakaguchi flask. After pre-culturing at 30° C. overnight, 1% aliquots of the culture broth was each inoculated to 75 ml of the same medium as described above in a Sakaguchi flask. Culturing was carried out at 30° C. for 18 hours with stirring at 120 rpm.

The combined cultures, measuring 1700 ml, was centrifuged at 10,000 rpm for 15 minutes. The supernatant was adjusted to pH 6.0 with hydrochloric acid, concentrated under reduced pressure, and allowed to stand at 5° C. overnight. The precipitated crystals were suspended in 450 ml of purified water, 25.2 g of potassium hydroxide added thereto, about 600 ml of dichloromethane further added thereto, and about 400 ml of an aqueous layer separated. Hydrochloric acid was added to the aqueous layer to precipitate crystals, followed by centrifugation (12,000 rpm×15 mins) to recover the solid. The solid was suspended in about 100 ml of water and again subjected to centrifugation. The solid recovered was mixed with about 80 ml of ethyl alcohol, followed by drying under reduced pressure at 50° C. to obtain a preparation weighing 1.18 g.

An aliquot of the preparation was analyzed as follows to determine the structure.
(a) Ethylation of the Preparation:
A 0.2 g aliquot of the preparation was dissolved in 1.7 ml of a 1N potassium hydroxide aqueous solution, followed by evaporation to dryness under reduced pressure. The residue was suspended in 1.5 ml of dimethylformamide, and 0.22 ml of ethyl bromide was added thereto while stirring. The mixture was heated at 90° C. for 5 hours with stirring.

Dimethylformamide was removed by distillation under reduced pressure. The residue was dissolved in 30 ml of dichloromethane, washed twice with 20 ml portions of a 1N potassium hydroxide aqueous solution and once with 20 ml of water, dried over anhydrous magnesium sulfate, dried under reduced pressure to remove dichloromethane, and finally dried in vacuo to obtain 0.2 g (yield: 88.1%) of an ethylated preparation.

(b) Preparation of 1-Ethyl-3,7-dimethylxanthine:

0.9 g of theobromine (a product of Amano Pharmaceutical Co., Ltd.) was dissolved in 7.5 ml of a 1N potassium hydroxide aqueous solution, followed by drying under reduced pressure. The residue was suspended in 6 ml of dimethylformamide, and 0.6 ml of ethyl bromide was added thereto while stirring, followed by heating at 90° C. for 8 hours while stirring.

Dimethylformamide was removed by distillation under reduced pressure, and the residue was dissolved in 50 ml of dichloromethane, washed twice with 30 ml portions of a 1N potassium hydroxide aqueous solution and once with 30 ml of water, dried over anhydrous magnesium sulfate, dried under reduced pressure to remove dichloromethane, and finally dried in vacuo to obtain 0.86 g (yield: 83%) of 1-ethyl-3,7-dimethylxanthine.

The $^{13}$C-NMR spectrum of the N-substituents of the ethylated preparation obtained in (a) (hereinafter referred to as (4)) was compared with those of caffeine (1,3,7-trimethylxanthine) (hereinafter referred to as (1)), 1-ethyl-3,7-dimethylxanthine obtained in (b) (hereinafter referred to as (2)), and 1,3-dimethyl-7-propylxanthine obtained in Reference Example 1 (hereinafter referred to as (3)). That is, by comparing the $^{13}$-NMR spectra of the N-methyl groups of (1), (2) and (3), the chemical shifts (ppm) of the N-methyl groups at the 1-, 3-, and 7-positions (hereinafter referred to as $N_1$-methyl, $N_3$-methyl, and $N_7$-methyl, respectively) were decided as follows.

$N_1$-methyl: 27.72 ppm $N_3$-methyl: 29.37–29.54 ppm $N_7$-methyl: 33.35–33.40 ppm Then, by comparing the chemical shifts of the $N_1$-methyl and N3-methyl of (3) (27.72 ppm and 29.48 ppm, respectively) with that of the N-methyl group of (4) (29.43 ppm), it was proved that the compound of the preparation is 3-methyl-7-propylxanthine, a product derived from (3) by release of the $N_1$-methyl group by microbial conversion. The results of the chemical shifts as above determined are shown in Table 1 below.

TABLE 1

| Assignment | (1) 1,3,7-trimethyl-xanthine | (2) 1-ethyl-3,7-di-methyl-xanthine | (3) 1,3-di-methyl-7-propyl-xanthine | (4) ethylated prepa-ration |
| --- | --- | --- | --- | --- |
| C$\underline{H}_3$CH$_2$CH$_2$ (N$_7$) | | | 10.62 | 10.62 |
| C$\underline{H}_3$CH$_2$ (N$_1$) | | 13.16 | | 13.06 |
| CH$_3$C$\underline{H}_2$CH$_2$ (N$_7$) | | | 23.97 | 23.97 |
| C$\underline{H}_3$ (N$_1$) | 27.72 | | 27.72 | |
| C$\underline{H}_3$ (N$_3$) | 29.54 | 29.37 | 29.48 | 29.43 |
| C$\underline{H}_3$ (N$_7$) | 33.40 | 33.35 | | |
| CH$_3$C$\underline{H}_2$ (N$_1$) | | 36.19 | | 36.30 |
| CH$_3$CH$_2$C$\underline{H}_2$ (N$_7$) | | | 48.57 | 48.57 |

Measurements of $^{13}$C-NMR spectrum were made under the following conditions:

Sample solution: 70 mg of (1) or 100 mg of (2), (3) or (4) in 0.5 ml of CDCl$_3$ Apparatus: JNM-FX60Q manufactured by Japan Electron Optics Lab. Co., Ltd.

Standard: chemical shift of CDCl$_3$, 77.1 ppm

EXAMPLE 2

*Pseudomonas cepacia* FERM BP-4282 was inoculated to a medium having the same composition as used in Example 1 and further containing 0.01% 7-methylxanthine or 0.1% theobromine. After pre-culturing at 30° C. overnight, 1% aliquots of the culture broth were each inoculated to 75 ml of the same medium as described above in a Sakaguchi flask. Culturing was carried out at 30° C. for 18 hours with stirring at 120 rpm.

The combined culture was analyzed by high performance liquid chromatography (HPLC) using a chromatograph manufactured by Toso Co., Ltd. As a result, a peak having the same retention time as that observed with the 3-methyl-7-propylxanthine (preparation) as obtained in Example 1 was confirmed, indicating accumulation of 3-methyl-7-propylxanthine in the culture. HPLC was conducted under the following conditions:

Column: ODS-80TM (manufactured by Toso Co., Ltd. )

Mobile phase: aqueous solution containing 17% acetonitrile and 0.1% trifluoroacetic acid Flow rate: 1 ml/min

EXAMPLE 3

In the same manner as in Example 2, *Pseudomonas putida* IF-3 (deposited as FERM BP-3824 under the Budapest Treaty) was pre-cultured at 30° C. overnight, and 1% aliquots of the culture broth was each inoculated to 75 ml of the same medium in a Sakaguchi flask. Culturing was carried out at 30° C. for 18 hours with stirring at 120 rpm.

As a result of HPLC analysis of the combined culture under the same conditions as in Example 2, production of 3-methyl-7-propylxanthine was confirmed.

EXAMPLE 4

*Pseudomonas putida* IF-3-9C-21 (deposited as FERM BP-3825 under the Budapest Treaty) was cultured in the same manner as in Example 1, except for removing 1,3-dimethyl-7-propylxanthine from the composition of the culture medium. The resulting culture broth was mixed with 1,3-dimethyl-7-propylxanthine, and the mixture was analyzed by HPLC under the same conditions as in Example 2. As a result, production of 3-methyl-7-propylxanthine was confirmed.

EXAMPLE 5

Isolation of Caffeine Demethylase Gene Originated in Caffeine-metabolizing Bacterium (1) Preparation of Caffeine Demethylase-deficient Mutant:

*Pseudomonas putida* IF-3-9C, a mutant strain which has the ability to assimilate caffeine constitutively and obtained from a parent strain IF-3 (deposited as FERM BP-3824 under the Budapest Treaty), was cultured in a TY medium (1.0% Bacto-tryptone and 0.5% Bacto-yeast extract) to the logarithmic growth phase. The microbial cells were collected by centrifugation, washed, and suspended in 5 ml of a 50 mM Tris-maleate buffer (pH=6.0).

NTG was added to the cell suspension to a final concentration of 100 μg/ml, and the suspension was allowed to stand at 30° C. for 30 minutes. After the NTG treatment, cells were washed twice with a 0.9% sodium chloride aqueous solution and then shake cultured at 30° C. overnight in a caffeine minimal medium (0.3% caffeine, 0.3% ammonium sulfate, 0.5% potassium secondary phosphate, 0.1% sodium chloride, and 0.2% magnesium sulfate heptahydrate; pH=7.0) to which carbenicillin had been added to a final concentration of 500 μg/ml. The collected cells were washed twice with a 0.9% sodium chloride aqueous solution.

The washed cells were suspended in 1 ml of a 0.9% sodium chloride aqueous solution, diluted appropriately, and spread on an LT-agar medium (1% Bacto-tryptone and 0.5% Bacto-yeast extract). After culturing at 30° C. for 1 day on the LT-agar medium, the colonies were replicated on a caffeine minimal medium. After culturing at 30° C. for 2 days, the assimilation properties for caffeine, theobromine, and 7-methylxanthine of the strains which showed poor growth in the caffeine minimal medium were examined, and a mutant strain IF-3-19 which assimilated theobromine and 7-methylxanthine but did not assimilate caffeine was obtained.

*Pseudomonas putida* IF-3-19 is a mutant strain which does not convert caffeine into theobromine, i.e., a caffeine demethylase-deficient mutant.

(2) Cloning of Caffeine Demethylase Gene:

The total DNA of *Pseudomonas putida* IF-3 (deposited as FERM BP-3824 under the Budapest Treaty) or *Pseudomonas flayida* IF-4 (deposited as FERM P-10865, FERM BP-4281 under the Budapest Treaty) was prepared in accordance with the method of Saito and Miura (see *Biochem. Biophys. Acta*, Vol. 72, pp 619–629 (1963)). The resulting total DNA was cleaved with HindIII to obtain fragments (about 1 μg). Using T4 DNA ligase, the fragment cut out was ligated to a cloning vector pNI20C (about 2 μg) which had been digested with HindIII and dephosphorylated.

*Pseudomonas putida* IF-3-19, a caffeine demethylase-deficient mutant, was subjected to transformation by using the resulting recombinant plasmid DNA, and spread on a caffeine minimal agar medium containing 25 μg/ml of kanamycin.

After culturing at 30° C. for 2 days, four transformant strains containing genes originated in *Pseudomonas putida* IF-3 and three transformant strains containing genes originated in *Pseudomonas flavida* IF-4 were obtained.

A plasmid was prepared from each transformant strain and digested with HindIII. The cleavage pattern was confirmed by agarose gel electrophoresis. It was revealed that all these strains had in common DNA fragments of from 2.4 kb and 4.3 kb DNA fragments shown in FIG. 1 which were cleaved with HindIII.

(3) Subcloning of Caffeine Demethylase and Position Determination Thereof:

One of the plasmids obtained in (2) above was designated pTF1. PTF1 was cleaved with various restriction enzymes and analyzed by agarose gel electrophoresis to furnish a restriction endonuclease cleavage map of the inserted 6.7 kb DNA fragment comprising as shown in FIG. 1. Then, in order to specify the caffeine demethylase coding region present in this fragment, each of the various DNA fragments digested with restriction enzymes was inserted and ligated to pNI107 to prepare a recombinant DNA, and *Pseudomonas putida* IF-3-19 was transformed with this recombinant DNA. As a result, an about 1.7 kb DNA fragment cut out by AccI and NdeI and made IF-3-19 restore caffeine assimilation properties was obtained. The plasmid with this DNA fragment was designated pCA32A.

(4) Confirmation of Caffeine Demethylase Gene Existing in pCA32A:

In order to confirm the fact that the DNA fragment inserted in pCA32A obtained in the steps up to (3) above codes caffeine demethylase, pCA32A was introduced into *Pseudomonas putida* ATCC 8209 having no assimilating properties for caffeine, and whether or not the resulting transformant was capable of converting caffeine into theobromine was examined. The details of the procedures were as follows.

pCA32A obtained in (3) above was introduced into *Pseudomonas putida* ATCC 8209 with no caffeine assimilation, i.e., no capability of assimilating any of caffeine, theobromine and 7-methylxanthine, to obtain a transformant 8209/pCA32A. For comparison, plasmid vector pNI107 was introduced into *P. putida* ATCC 8209 to obtain a transformant 8209/pNI107.

Each of the resulting transformant strains was inoculated to 5 ml of a TYKG medium (1.5% Bacto-tryptone, 0.75% Bacto-yeast extract, 0.5% potassium secondary phosphate, 0.2% glucose, and 25 μg/ml kanamycin; pH=6.7) and shake cultured at 30° C. for 8 hours. A 0.5 ml portion of the culture broth was inoculated to 50 ml of a TYKG medium in each of ten 500-ml Sakaguchi flasks, followed by shake culturing at 30° C. for 16 hours.

The resulting cultures were combined (500 ml) and centrifuged at 7,000 rpm for 10 minutes. The microbial cells thus collected were washed with a 20 mM sodium phosphate buffer (pH=6.0) and suspended in 30 ml of the same buffer.

To the cell suspension (0.5 ml) were added 105 μl of a 100 mM caffeine aqueous solution, 210 μl of a 50 mM NADH aqueous solution, 50 μl of a 0.8M sodium phosphate buffer, and 1135 ml of water, and the system was allowed to react at 25° C. for 16 hours. A 475 μl aliquot of the reaction mixture was added to 25 μl of a 50% trichloroacetic acid aqueous solution to stop the reaction. The mixture was centrifuged, and caffeine and theobromine contents in the supernatant liquor were determined by HPLC under the following conditions to evaluate caffeine demethylase activity. The results obtained are shown in Table 2.

Column: ODS-80TM, manufactured by Toso Co., Ltd.

Mobile phase: aqueous solution containing 17% acetonitrile and 0.1% trifluoroacetic acid Flow rate: 1 ml/min Detection: 272 nm

TABLE 2

| Transformant Strain | Reaction Time | | | |
| --- | --- | --- | --- | --- |
| | 0 Hr | | 17 Hrs. | |
| | Caffeine (mg/ml) | Theobromine (mg/ml) | Caffeine (mg/ml) | Theobromine (mg/ml) |
| Pseudomonas putida ATCC8209/pNI107 | 0.94 | 0 | 0.94 | 0 |
| Pseudomonas putida ATCC8209/pCA32A | 0.938 | 0 | 0.763 | 0.160 |

As is shown in Table 2, the strain having been transformed with a plasmid vector pNI107 produced no theobromine, while the transformant of ATCC 8209 with pCA32A converted 18.6% of the caffeine substrate to produce 0.16 g/l of theobromine. These results prove that the inserted DNA fragment of pCA32A contains a caffeine demethylase gene.

(5) Sequence Determination of Caffeine Demethylase Gene:

The base sequence of the AccI-NdeI DNA fragment of about 1.7 kb which had been inserted into pCA32A was determined in accordance with the Sanger method. More specifically, the end of the DNA fragment cut out by AccI and NdeI was blunt-ended by a Klenow fragment and inserted into pUC118 at the SmaI recognition site to obtain plasmids 118A and 118B different in insertion direction.

From the resulting plasmid were prepared plasmids in which the inserted DNA fragment were stepwise deleted by means of a Deletion Kit produced by Takara Shuzo Co., Ltd. A complementary DNA was synthesized using each of the deletion plasmids as a template by means of a Sequence Kit produced by Applied Biosystems Co. The base sequence was read out by a DNA sequencer. As a result, it was found that there is only one open reading frame in the above DNA fragment.

In SEQ ID NO:1, the DNA base sequence between AccI and NdeI (1686 bp) containing caffeine demethylase gene-containing DNA is shown. The presumed amino acid sequence of caffeine demethylase is also shown under each triplet of the bases.

EXAMPLE 6

Production of 3-Methyl-7-alkylxanthine from 1,3-Dimethyl-7-alkylxanthine by pCA32A Transformant

*Pseudomonas putida* IF-3-9C-21 (deposited as FERM BP-3825 under the Budapest Treaty) was transformed by pCA32A to obtain *P. putida* IF-3-9C-21/pCA32A.

*P. putida* IF-3-9C-21/pCA32A was inoculated to 75 ml of a medium (pH=6.7) containing 0.5% meat extract (produced by Kyokuto Seiyaku Kogyo Co., Ltd.), 0.3% Meast P1G (produced by Asahi Breweries, Ltd.), and 0.3% potassium secondary phosphate in a 500 ml Sakaguchi flask and pre-cultured at 30° C. for 16 hours. In a 5 l mini-jar was put 2 l of the above medium, and 0.5% 1,3-dimethyl-7-ethylxanthine, 1,3-dimethyl-7-propylxanthine or 1,3-dimethyl-7-butylxanthine was added thereto. One percent of the pre-culture broth was inoculated to the prepared medium and cultured for 24 to 48 hours at a temperature controlled at 30° C. for the first 7 hours and then at 25° C. with aeration at 1 v.v.m and stirring at 600 rpm by means of a flat type turbine agitator with six blades. From after 4 hours from the commencement of culturing, the pH of the culture was controlled between 6.6 and 6.8 and feeding of a medium having the following composition was started.

| Medium Composition to be fed: | |
| --- | --- |
| Glucose | 17% |
| Sodium glutamate | 2% |
| Meat extract | 4% |
| Meast P1G | 4% |

As shown in Table 3 below, production of the corresponding 1-demethylated compound was observed in each culture.

TABLE 3

| Substrate | Substrate Concn. (mg/ml) | Culture Period (hr) | Product | Product Concn. (mg/ml) |
| --- | --- | --- | --- | --- |
| 1,3-dimethyl-7-ethylxanthine | 5.20 | 24 | 3-methyl-7-ethylxanthine | 4.65 |
| 1,3-dimethyl-7-propylxanthine | 5.26 | 24 | 3-methyl-7-propylxanthine | 4.98 |
| 1,3-dimethyl-7-butylxanthine | 4.20 | 48 | 3-methyl-7-butylxanthine | 1.80 |

EXAMPLE 7

Conversion of Caffeine to Theobromine and Conversion of 1,3-Dimethyl-7-propylxanthine to 3-Methyl-7-propylxanthine by *P. putida* IF-3-9C-21/pCA32A Each of *Pseudomonas putida* IF-3-9C-21 and *P. putida* IF-3- 9C-21/pCA32A was shake-cultured at 30° C. overnight in 75 ml of a medium containing 0.5% meat extract, 0.3% Meast P1G, and 0.3% potassium secondary phosphate (pH=6.7) in a 500 ml Sakaguchi flask. The medium used for the transformant strain further contained 25 μg/ml of kanamycin.

One percent of the resulting pre-culture was inoculated to 3 l of a medium containing 0.5% meat extract, 0.1% glucose, and 0.3% Meast P1G and further containing 0.5% caffeine or 1,3-dimethyl-7-propylxanthine and cultured for 50 hours at a temperature controlled at 30° C. for the first 7 hours and then at 25° C. with aeration at 1 v.v.m and stirring at 600 rpm by means of a flat type turbine agitator with 6 blades. From after 4 hours from the commencement of culturing, the pH of the culture was controlled between 6.6 and 6.8, and from the same time point, a medium comprising 25% glucose, 6% meat extract, 6% Meast P1G, 3% sodium glutamate, and 1.0% caffeine or 1,3-dimethyl-7-propylxanthine was started to be fed at a rate of 12 ml/hr.

The concentration of caffeine or 1,3-dimethyl-7-propylxanthine in the culture was measured with time, and these substrates were added appropriately so as to control the respective concentration between 0.5 and 2.5 mg/ml.

Figure 2:
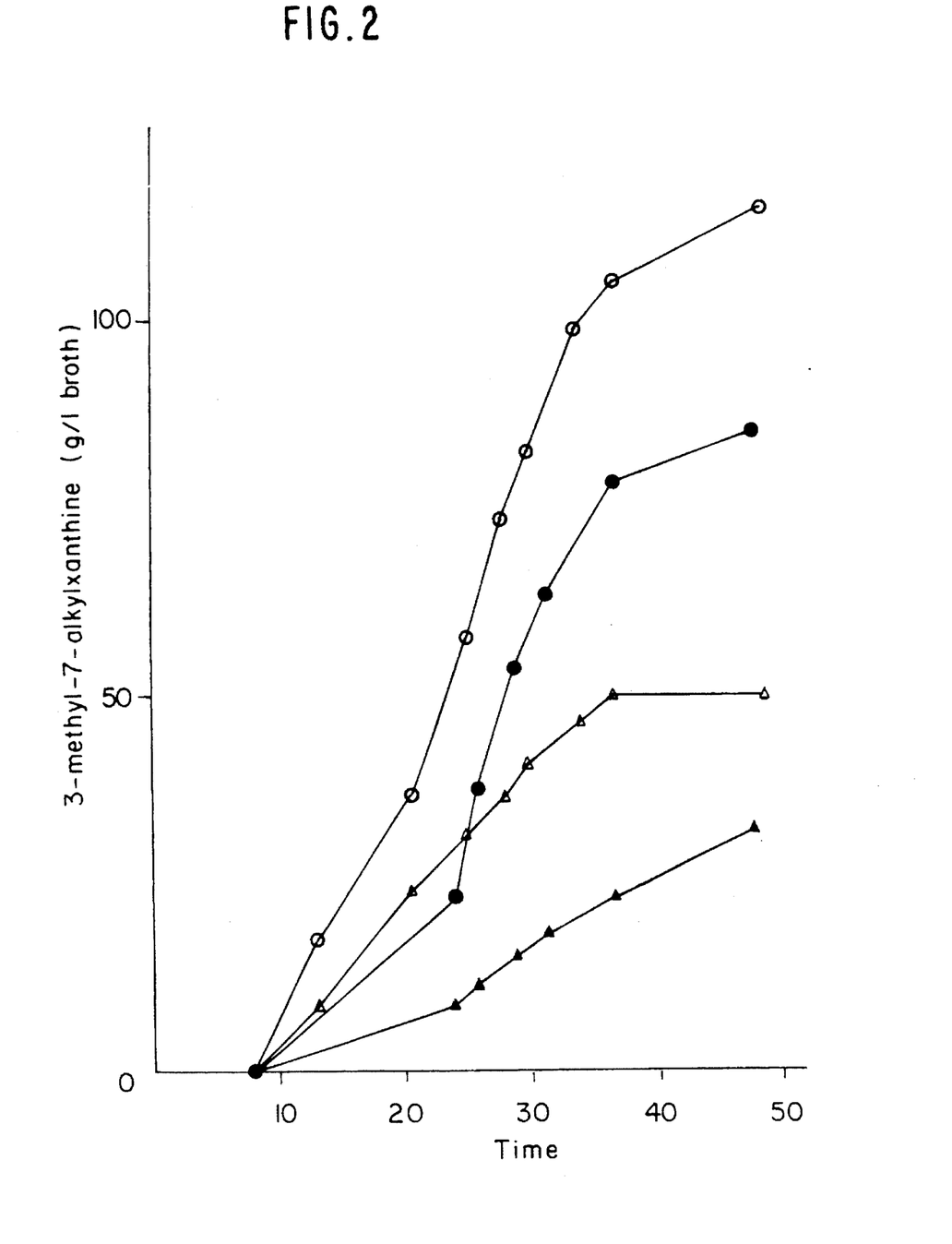
FIG. 2 is a graph showing the culture progress in a mini-jar. In the figure, white circles indicate production of theobromine by *Pseudomonas putida* IF-3-9C-21/pCA32A; white triangles production of theobromine by *Pseudomonas putida* IF- 3-9C-21; black circles production of 3-methyl-7-propylxanthine by *Pseudomonas putida* IF-3-9C-21/pCA32A; and black triangles production of 3-methyl-7-propylxanthine by *Pseudomonas putida* IF-3-9C-21, respectively.

The 1,3-methyl-7-alkylxanthine was thus converted to the corresponding 3-methyl-7-alkylxanthine. The results of the conversion reaction are shown in FIG. 2. It is seen that in using either of the substrates (caffeine or 1,3-dimethyl-7-propylxanthine) the transformant strain having pCA32A, i.e., *P. putida* IF-3-9C-21/pCA32A, produces the corresponding conversion product (theobromine or 3-methyl-7-propylxanthine, respectively) in an amount about 2 to 4 times that produced by *P. putida* IF-3-9C-21.

The amounts of the substrate and the product at the end of the culturing were measured. As a result, in the system of using *P. putida* IF-3-9C-21/pCA32A and caffeine as a substrate, a cumulative amount of caffeine added up to 50 hours was 535 g, while the residual caffeine was 80 g with production of 414 g of theobromine, indicating a caffeine to theobromine conversion of 98.9%. In the system of using the same strain and 1,3-dimethyl-7-propylxanthine as a substrate, a cumulative amount of the substrate added up to 50 hours was 350 g, while the residual substrate was 63 g with production of 262 g of 3-methyl-7-propylxanthine, indicating 1,3-dimethyl-7-propylxanthine to 3-methyl-7-propylxanthine conversion of 97%.

According to the present invention, a 3-methyl-7-alkylxanthine which is an important intermediate for pharmaceuticals can be produced efficiently and at low cost by culturing a microorganism capable of producing a 3-methyl-7-alkylxanthine or a mutant thereof in a nutrient medium containing a 1,3-dimethyl-7-alkylxanthine to produce and accumulate a 3-methyl-7-alkylxanthine in the culture and recovering the same from the culture.

The present invention provides a DNA fragment containing a caffeine demethylase gene, which makes it possible to provide a novel *Pseudomonas putida* strain having enhanced caffeine demethylase activity in catalyzing demethylation of caffeine at the 1-position thereof. Use of the novel *P. putida* strain makes it possible to produce a 3-methyl-7-alkylxanthine from the corresponding 1,3-dimethyl-7-alkylxanthine at further improved efficiency.

While the invention has been described in detail and with reference to specific examples thereof, it will be apparent to one skilled in the art that various changes and modifications can be made therein without departing from the spirit and scope thereof.

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 1686 base pairs
        ( B ) TYPE: nucleic acid
        ( C ) STRANDEDNESS: double
        ( D ) TOPOLOGY: linear     ( i i ) MOLECULE TYPE: DNA (genomic)

( i x ) FEATURE:
        ( A ) NAME/KEY: CDS
        ( B ) LOCATION: 476..1528

( x i ) SEQUENCE DESCRIPTION: SEQ ID NO:1:

```
GTAGACTGTC  TTTACGCCCC  GCACATTCTC  TATCGTAAAA  ATTTCCACGC  TGAGCCCACG         60

CTAATTTAAT  CAAGTCTCAT  TCAACTGAGC  CGCACAGCCG  CGTGTCATTG  AGTGATCACC        120

GGCAGTAACA  TTTTACGGCT  GAGCGGCTTG  CAGCAATGTT  TCTTTTATGC  ACCAAACTCG        180

CCCACCTAAT  GCACTAAATC  GAACCATTAA  AAACTTAGCT  AATACTCTAA  AATCTATTGG        240

ATTTGACCAC  TTACATTTTT  AACCGTCCAG  AGCCTATCCG  AAGTTGACAC  GCGGGTCAGA        300

AATGGCCTAT  TTTTTCTTTG  TGTACCAGAT  GATAAATCTG  ATGTACCAGC  CGTATGATTG        360

GCGTAAATAC  ACCATTACCA  AGTGTTTACC  CTTTCTATGA  GTAGATGTAG  GAGACAGGGC        420

ACTCAGCTGA  GTTGAGTGTT  CATACATAAC  AACGTCATCC  ACAAAGGCTA  CATAC ATG         478
                                                                  Met
                                                                  1

GAA CAG ACA ATC AAT AAC AAC GAT CGC GAG TAC CTT CGG CAC TTT TGG             526
Glu Gln Thr Ile Asn Asn Asn Asp Arg Glu Tyr Leu Arg His Phe Trp
            5                   10                  15

CAT CCC GTC TGT ACA GTG ACA GAA CTG GAA AAG GCC CAC CCC TCC AGC             574
His Pro Val Cys Thr Val Thr Glu Leu Glu Lys Ala His Pro Ser Ser
        20                  25                  30

CTA GGC CCA ATA GGG GTG AAG CTT CTA AAT GAG CAA TTG GTT GTT GCT             622
Leu Gly Pro Ile Gly Val Lys Leu Leu Asn Glu Gln Leu Val Val Ala
    35                  40                  45

AAA CTT AGT GGC CAA TAC GTC GCA ATG CAT GAT CGC TGC GCA CAT CGG             670
Lys Leu Ser Gly Gln Tyr Val Ala Met His Asp Arg Cys Ala His Arg
50                  55                  60                  65

TCG GCA AAG CTC TCC CTG GGC ACC ATC GCT AAT GAT CGA CTG CAA TGC             718
Ser Ala Lys Leu Ser Leu Gly Thr Ile Ala Asn Asp Arg Leu Gln Cys
                70                  75                  80

CCT TAT CAT GGG TGG CAG TAC GAC ACG GAA GGT GCA TGT AAA CTA GTG             766
Pro Tyr His Gly Trp Gln Tyr Asp Thr Glu Gly Ala Cys Lys Leu Val
            85                  90                  95

CCG GCG TGC CCC AAC AGC CCC ATT CCT AAT CGA GCT AAA GTT CAG CGA             814
Pro Ala Cys Pro Asn Ser Pro Ile Pro Asn Arg Ala Lys Val Gln Arg
        100                 105                 110

TTC GAT TGT GAA GAG CGG TAC GGT CTG ATT TGG GTA AGG CTG GAC TCA             862
Phe Asp Cys Glu Glu Arg Tyr Gly Leu Ile Trp Val Arg Leu Asp Ser
```

-continued

```
                 115                           120                            125
AGT  TAT  GCT  TGC  ACT  GAG  ATC  CCA  TAC  TTC  AGT  GCA  GCA  AGC  GAT  CCG        910
Ser  Tyr  Ala  Cys  Thr  Glu  Ile  Pro  Tyr  Phe  Ser  Ala  Ala  Ser  Asp  Pro
130                      135                      140                      145

AAA  CTT  CGA  GTC  GTG  ATC  CAA  GAA  CCC  TAT  TGG  TGG  AAC  GCA  ACA  GCA        958
Lys  Leu  Arg  Val  Val  Ile  Gln  Glu  Pro  Tyr  Trp  Trp  Asn  Ala  Thr  Ala
                    150                      155                           160

GAG  CGA  CGT  TGG  GAA  AAC  TTT  ACA  GAC  TTT  TCC  CAT  TTT  GCG  TTT  ATC       1006
Glu  Arg  Arg  Trp  Glu  Asn  Phe  Thr  Asp  Phe  Ser  His  Phe  Ala  Phe  Ile
               165                      170                      175

CAC  CCT  GGC  ACG  CTG  TTT  GAT  CCT  AAC  AAC  GCG  GAA  CCG  CCG  ATC  GTA       1054
His  Pro  Gly  Thr  Leu  Phe  Asp  Pro  Asn  Asn  Ala  Glu  Pro  Pro  Ile  Val
          180                      185                      190

CCG  ATG  GAT  CGT  TTT  AAT  GGC  CAA  TTC  CGT  TTC  GTT  TAC  GAT  ACC  CCG       1102
Pro  Met  Asp  Arg  Phe  Asn  Gly  Gln  Phe  Arg  Phe  Val  Tyr  Asp  Thr  Pro
     195                      200                      205

GAA  GAT  ATG  GCC  GTT  CCA  GAT  CAA  GCC  CCA  ATT  GGG  TCG  TTC  TCT  TAT       1150
Glu  Asp  Met  Ala  Val  Pro  Asp  Gln  Ala  Pro  Ile  Gly  Ser  Phe  Ser  Tyr
210                      215                      220                      225

ACC  TGC  AGC  ATG  CCC  TTC  GCT  ATC  AAT  CTG  GAA  GTC  GCT  AAG  TAC  TCA       1198
Thr  Cys  Ser  Met  Pro  Phe  Ala  Ile  Asn  Leu  Glu  Val  Ala  Lys  Tyr  Ser
                    230                      235                      240

AGC  AAT  TCA  TTG  CAT  GTG  CTT  TTC  AAC  GTG  TCA  TGC  CCA  GTT  GAC  GAT       1246
Ser  Asn  Ser  Leu  His  Val  Leu  Phe  Asn  Val  Ser  Cys  Pro  Val  Asp  Asp
                    245                      250                      255

AGC  ACT  ACC  AAG  AAC  TTC  TTG  CTG  TTC  GCA  AGG  GAG  CAG  GCT  GAC  GAT       1294
Ser  Thr  Thr  Lys  Asn  Phe  Leu  Leu  Phe  Ala  Arg  Glu  Gln  Ala  Asp  Asp
          260                      265                      270

TCA  GAT  TAT  CTT  CAC  ATT  GCA  TTT  AAT  GAT  TTA  GTC  TTT  GCT  GAA  GAT       1342
Ser  Asp  Tyr  Leu  His  Ile  Ala  Phe  Asn  Asp  Leu  Val  Phe  Ala  Glu  Asp
     275                      280                      285

AAG  CCT  GTG  ATC  GAG  TCT  CAA  TGG  CCG  AAG  GAT  GCT  CCG  GCT  GAT  GAA       1390
Lys  Pro  Val  Ile  Glu  Ser  Gln  Trp  Pro  Lys  Asp  Ala  Pro  Ala  Asp  Glu
290                      295                      300                      305

GTT  TCG  GTT  GTC  GCG  GAT  AAA  GTC  TCG  ATC  CAG  TAT  AGA  AAA  TGG  CTG       1438
Val  Ser  Val  Val  Ala  Asp  Lys  Val  Ser  Ile  Gln  Tyr  Arg  Lys  Trp  Leu
                    310                      315                      320

CGG  GAA  CTG  AAA  GAG  GCC  CAT  CAA  GAC  GGT  GCT  CAG  GCT  TTC  CGT  AGT       1486
Arg  Glu  Leu  Lys  Glu  Ala  His  Gln  Asp  Gly  Ala  Gln  Ala  Phe  Arg  Ser
               325                      330                      335

GCG  TTG  CTG  GAC  TCC  GTG  ATC  GAG  AGC  GAT  CGA  AGC  TAC  ACC                 1528
Ala  Leu  Leu  Asp  Ser  Val  Ile  Glu  Ser  Asp  Arg  Ser  Tyr  Thr
          340                      345                      350

TAACATTTGC  GTATGAGGGT  GGCGCACTGC  GCCTTTTTTT  TTAGGGTCAA  AAAAAGACGG       1588

CCTCCTAGGA  GGCCGTAAAC  TCGCTACGTC  CAACTCGTAT  TAGGGCTTCT  TGAATGAATA       1648

GACAGCCAAT  TTGTTCCCGT  CGAGATCGCG  CACATATG                                 1686
```

( 2 ) INFORMATION FOR SEQ ID NO:2:

( i ) SEQUENCE CHARACTERISTICS:
     ( A ) LENGTH: 351 amino acids
     ( B ) TYPE: amino acid
     ( D ) TOPOLOGY: linear ( i i ) MOLECULE TYPE: protein ( x i ) SEQUENCE DESCRIPTION: SEQ ID NO:2:

```
Met  Glu  Gln  Thr  Ile  Asn  Asn  Asn  Asp  Arg  Glu  Tyr  Leu  Arg  His  Phe
 1              5                        10                       15

Trp  His  Pro  Val  Cys  Thr  Val  Thr  Glu  Leu  Glu  Lys  Ala  His  Pro  Ser
```

|  |  |  |  |  | 20 |  |  |  | 25 |  |  |  | 30 |  |
|---|---|---|---|---|---|---|---|---|---|---|---|---|---|---|
| Ser | Leu | Gly<br>35 | Pro | Ile | Gly | Val | Lys<br>40 | Leu | Leu | Asn | Glu | Gln<br>45 | Leu | Val | Val |
| Ala | Lys<br>50 | Leu | Ser | Gly | Gln | Tyr<br>55 | Val | Ala | Met | His | Asp<br>60 | Arg | Cys | Ala | His |
| Arg<br>65 | Ser | Ala | Lys | Leu | Ser<br>70 | Leu | Gly | Thr | Ile | Ala<br>75 | Asn | Asp | Arg | Leu | Gln<br>80 |
| Cys | Pro | Tyr | His | Gly<br>85 | Trp | Gln | Tyr | Asp | Thr<br>90 | Glu | Gly | Ala | Cys | Lys<br>95 | Leu |
| Val | Pro | Ala | Cys<br>100 | Pro | Asn | Ser | Pro | Ile<br>105 | Pro | Asn | Arg | Ala | Lys<br>110 | Val | Gln |
| Arg | Phe | Asp<br>115 | Cys | Glu | Glu | Arg | Tyr<br>120 | Gly | Leu | Ile | Trp | Val<br>125 | Arg | Leu | Asp |
| Ser | Ser<br>130 | Tyr | Ala | Cys | Thr | Glu<br>135 | Ile | Pro | Tyr | Phe | Ser<br>140 | Ala | Ala | Ser | Asp |
| Pro<br>145 | Lys | Leu | Arg | Val | Val<br>150 | Ile | Gln | Glu | Pro | Tyr<br>155 | Trp | Trp | Asn | Ala | Thr<br>160 |
| Ala | Glu | Arg | Arg | Trp<br>165 | Glu | Asn | Phe | Thr | Asp<br>170 | Phe | Ser | His | Phe | Ala<br>175 | Phe |
| Ile | His | Pro | Gly<br>180 | Thr | Leu | Phe | Asp | Pro<br>185 | Asn | Asn | Ala | Glu | Pro<br>190 | Pro | Ile |
| Val | Pro | Met<br>195 | Asp | Arg | Phe | Asn | Gly<br>200 | Gln | Phe | Arg | Phe | Val<br>205 | Tyr | Asp | Thr |
| Pro | Glu<br>210 | Asp | Met | Ala | Val | Pro<br>215 | Asp | Gln | Ala | Pro | Ile<br>220 | Gly | Ser | Phe | Ser |
| Tyr<br>225 | Thr | Cys | Ser | Met | Pro<br>230 | Phe | Ala | Ile | Asn | Leu<br>235 | Glu | Val | Ala | Lys | Tyr<br>240 |
| Ser | Ser | Asn | Ser | Leu<br>245 | His | Val | Leu | Phe | Asn<br>250 | Val | Ser | Cys | Pro | Val<br>255 | Asp |
| Asp | Ser | Thr | Thr<br>260 | Lys | Asn | Phe | Leu | Leu<br>265 | Phe | Ala | Arg | Glu | Gln<br>270 | Ala | Asp |
| Asp | Ser | Asp<br>275 | Tyr | Leu | His | Ile | Ala<br>280 | Phe | Asn | Asp | Leu | Val<br>285 | Phe | Ala | Glu |
| Asp | Lys<br>290 | Pro | Val | Ile | Glu | Ser<br>295 | Gln | Trp | Pro | Lys | Asp<br>300 | Ala | Pro | Ala | Asp |
| Glu<br>305 | Val | Ser | Val | Val | Ala<br>310 | Asp | Lys | Val | Ser | Ile<br>315 | Gln | Tyr | Arg | Lys | Trp<br>320 |
| Leu | Arg | Glu | Leu | Lys<br>325 | Glu | Ala | His | Gln | Asp<br>330 | Gly | Ala | Gln | Ala | Phe<br>335 | Arg |
| Ser | Ala | Leu | Leu<br>340 | Asp | Ser | Val | Ile | Glu<br>345 | Ser | Asp | Arg | Ser | Tyr<br>350 | Thr |  |

What is claimed is:

1. A process for producing a 3-methyl-7-alkylxanthine represented by formula (II):

(II)

wherein R represents a straight-chain or branched alkyl group, comprising cultivating a transformant in a nutrient culture medium containing a 1,3-dimethyl-7-alkylxanthine represented by formula (I):

(I)

wherein R is as defined above, to produce 3-methyl-7-alkylxanthine in the resulting culture and recovering the produced 3-methyl-7-alkylxanthine from the culture, wherein said transformant comprises an organism of the genus Pseudomonas which has the ability to constitutively convert caffeine into theobromine, but lacks the ability to demethylate theobromine into 7-methylxanthine, that has been transformed with a recombinant DNA vector comprising a DNA molecule encoding a caffeine demethylase gene of a microorganism belonging to the genus Pseudomonas, which has the ability to assimilate caffeine, and wherein said transformant produces caffeine demethylase during said cultivating.

2. A process for producing a 3-methyl-7-alkylxanthine represented by formula (II):

wherein R represents a straight-chain or branched alkyl group, comprising cultivating a transformant in a nutrient culture medium, adding 1,3-dimethyl-7-alkylxanthine represented by formula (I):

wherein R is as defined above, to the culture medium to produce 3-methyl-7-alkylxanthine and recovering the produced 3-methyl-7-alkylxanthine, wherein said transformant comprises an organism of the genus Pseudomonas which has the ability to constitutively convert caffeine into theobromine, but lacks the ability to demethylate theobromine into 7-methylxanthine, that has been transformed with a recombinant DNA vector comprising a DNA molecule encoding a caffeine demethylase gene of a microorganism belonging to the genus Pseudomonas, which has the ability to assimilate caffeine, and wherein said transformant produces caffeine demethylase during said cultivating.

3. The process as claimed in claim 1 or 2, wherein R is a $C_1$–$C_4$ alkyl group.

4. A process for producing a 3-methyl-7-propylxanthine represented by formula (IV):

comprising cultivating a microorganism of the genus Pseudomonas, which produces caffeine demethylase capable of converting 1,3-dimethyl-7-propylxanthine to 3-methyl-7-propylxanthine, wherein said microorganism produces caffeine demethylase during said cultivating, in a nutrient culture medium containing 1,3-dimethyl-7-propylxanthine represented by formula (III):

to produce the 3-methyl-7-propylxanthine of formula (IV) in the culture and recovering the produced 3-methyl-7-propylxanthine of formula (IV) from the culture.

5. A process for producing a 3-methyl-7-propylxanthine represented by formula (IV):

comprising cultivating in a nutrient culture medium a microorganism of the genus Pseudomonas, which during the cultivating produces caffeine demethylase capable of converting 1,3-dimethyl-7-propylxanthine to 3-methyl-7-propylxanthine, adding 1,3-dimethyl-7-propylxanthine represented by formula (III):

to the culture medium to produce the 3-methyl-7-propylxanthine of formula (IV), and recovering the produced 3-methyl-7-propylxanthine of formula (IV).

6. The process as claimed in claim 4 or 5, wherein said microorganism is *Pseudomonas putida*.

7. The process as claimed in claim 6, wherein said microorganism is *Pseudomonas putida* IF-3-9C-21 (FERM BP-3825).

8. The process as claimed in claim 1 or 2, wherein said DNA molecule is defined by the restriction endonuclease cleavage map shown in FIG. 1.

9. The process as claimed in claim 8, wherein the base sequence between the AccI site and NdeI in the restriction endonuclease cleavage map of FIG. 1 which encodes the caffeine demethylase gene is represented by SEQ ID NO: 1.

10. The process as claimed in claim 9, wherein said caffeine demethylase gene codes for the amino acid sequence represented by SEQ ID NO: 2.

* * * * *